US005854010A

United States Patent [19]

Denison et al.

[11] Patent Number: 5,854,010
[45] Date of Patent: Dec. 29, 1998

[54] BIOASSAY FOR DETECTING 2,3,7,8-TETRACHLORODIBENZO-PARA-DIOXIN AND TCDD-LIKE COMPOUNDS AND NOVEL RECOMBINANT CELL LINE USEFUL THEREFOR

[76] Inventors: Michael S. Denison, 1520 Rehrmann Dr., Dixon, Calif. 95620; Abraham Brouwer, Diedenweg 24, 6703 GX Wageningen, Netherlands; George C. Clark, 310 Alcona Ave., Durham, N.C. 27703

[21] Appl. No.: 813,321

[22] Filed: Mar. 10, 1997

[51] Int. Cl.⁶ .............................. C12Q 1/66; C12N 5/18; C07O 319/02
[52] U.S. Cl. ................................ 435/8; 435/354; 549/359
[58] Field of Search ......................... 435/8, 354; 549/359

[56] References Cited

U.S. PATENT DOCUMENTS

| | | | |
|---|---|---|---|
| 4,238,472 | 12/1980 | Albro et al. | 436/540 |
| 4,798,807 | 1/1989 | Vanderlaan et al. | 530/388.9 |
| 4,865,972 | 9/1989 | Hunter | 435/7.21 |
| 5,128,244 | 7/1992 | Poland et al. | 735/7.8 |
| 5,378,822 | 1/1995 | Bradfield et al. | 536/23.5 |
| 5,429,925 | 7/1995 | Vanderlaan et al. | 435/7.1 |
| 5,476,953 | 12/1995 | Clardy et al. | 549/364 |
| 5,484,709 | 1/1996 | Friedman et al. | 435/7.93 |
| 5,496,703 | 3/1996 | Babish et al. | 435/7.21 |

OTHER PUBLICATIONS

Garrison et al. Species–specific recombinant cell lines as bioassay systems for the detection of 2,3,7,8–tetrachlorodibenzo–p–dioxin–like chemicals. Fund. and Appl. Toxicol. vol. 30 pp. 194–203, 1996.

El–Fouly et al. Production of a novel recombinant cell line for use as a bioassay system for detection of 2,3,7,8–tetrachlorodibenzo–p–dioxin–like chemixals. Environ. Toxicol. and Chem. vol. 13 pp. 1581–1588, 1994.

Aarts et al. Species–specific antagonism of Ah receptor action by 2,2',5,5'–tetrachloro–and 2,2'3,3',4,4' hexachlorobiphenyl. Eur. J. Pharmacol. Environ. Toxicol. and Pharmacol. Sect. 293 pp. 463–474, 1995.

Klein–Hitpass et al., "A 13 bp Palindrome is a Functional Estrogen Responsive Element and Interacts Specifically with Estrogen Receptor", *Nucleic Acids Research*, vol. 16, No. 2, (1988) pp. 647–663.

Tanabe et al., "Highly Toxic Coplanar PCBs: Occurrence, Source, Persistency and Toxic Implications to Wildlife and Humans", *Environmental Pollution*, vol. 47, (1987) pp. 147–163.

Searle et al., "Building a Metal–Responsive Promoter with Synthetic Regulatory Elements", *Molecular and Cellular Biology*, vol. 5, No. 6, (1985) pp. 1480–1489.

Pons et al., "A New Cellular Model of Response to Estrogens: A Bioluminescent Test to Characterize (Anti)Estrogen Molecules", *BioTechniques*, vol. 9, No. 4, (1990) pp. 450–459.

Motojima, "Peroxisome Proliferator–Activated Receptor (PPAR): Structure, Mechanism of Activation and Diverse Functions", *Cell Structure and Function*, vol. 18, (1993) pp. 267–275.

Lee et al., "Functional Analysis of the Steroid Hormone Control Region of Mouse Mammary Tumor Virus", *Nucleic Acids Research*, vol. 12, No. 10, (1984) pp. 4191–4206.

Nelson et al., "P450 Superfamily: Update on New Sequences, Gene Mapping, Accession Numbers and Nomenclature", *Pharmacogenetics*, vol. 6, (1996) pp. 1–42.

Chen et al., "Subunit Composition of the Heteromeric Cytosolic Aryl Hydrocarbon Receptor Complex", *The Journal of Biological Chemistry*, vol. 269, No. 44, (1994) pp. 27554–27558.

Hord et al., "Physicochemical and Immunocytochemical Analysis of the Aryl Hydrocarbon Receptor Nuclear Translocator: Characterization of Two Monoclonal Antibodies to the Aryl Hydrocarbon Receptor Nuclear Translocator", *Molecular Pharmacology*, vol. 46, (1994) pp. 618–626.

Hahn et al., "Cytochrome P4501A Induction and Inhibition by 3,3', 4, 4'–Tetrachlorobiphenyl in an Ah Receptor–containing Fish Hepatoma Cell Line (PLHC–1)", *Aquatic Toxicology*, vol. 26, (1993) pp. 185–208.

Probst et al., "Role of the Aryl Hydrocarbon Receptor Nuclear Translocator Protein in Aryl Hydrocarbon (Dioxin) Receptor Action", *Molecular Pharmacology*, vol. 44, (1993) pp. 511–518.

Sawyer et al., "PCB Isomers and Congeners: Induction of Aryl Hydrocarbon Hydroxylase and Ethoxyresorufin O–Deethylase Enzyme Activities in Rat Hepatoma Cells", *Toxicology Letters*, vol. 13, (1982) pp. 87–93.

Denison et al., "The DNA Recognition Site for the Dioxin–Ah Receptor Complex", *The Journal of Biological Chemistry*, vol. 263, No. 33, (Nov., 1988) pp. 17221–17224.

Aarts et al., "Species–Specific Antagonism of Ah Receptor Action by 2,2'5,5'–Tetrachloro–and 2,2',3,3',4,4'–Hexachlorobiphenyl", *European Journal of Pharmacology, Environmental and Toxicology Section 293*, (1995) pp. 463–474.

Alam et al., "Reporter Genes: Application to the Study of Mammalian Gene Transcription", *Analytical Biochemistry*, vol. 188, (1990) pp. 245–254.

Kennedy et al., "Ethoxyresorufin–O–deethylase and Porphyrin Analysis in Chicken Embryo Hepatocyte Cultures with a Fluorescence Multiwell Plate Reader", *Analytical Biochemistry*, vol. 211, (1993) pp. 102–112.

(List continued on next page.)

Primary Examiner—George C. Elliott
Assistant Examiner—John S. Brusca
Attorney, Agent, or Firm—Jenkins & Wilson, P.A.

[57] ABSTRACT

A recombinant cell line deposited at the American Type Culture Collection under ATCC accession number CRL-12286, also known as the mouse H1L1.1 cell line, has been made by using genetic engineering techniques for inserting dioxin responsive elements upstream of a luciferase reporter gene, and then, transfecting the resultant recombinant expression plasmid, identified as pGudLuc1.1, into mouse hepatoma cells. The mouse H1L1.1 cell line is useful in a method for the quantitative analysis of polyaromatic hydrocarbons in samples.

31 Claims, 8 Drawing Sheets

OTHER PUBLICATIONS

Garrison et al., "Species–Specific Recombinant Cell Lines as Bioassay Systems for the Detection of 2,3,7,8–Tetrachlorodibenzo–p–dioxin–like Chemicals", *Fundamental and Applied Toxicology*, vol. 30, No. 2, (Apr., 1996) pp. 194–203.

El–Fouly et al., "Production of a Novel Recombinant Cell Line for Use as a Bioassay System for Detection of 2,3 7,8–Tetrachlorodibenzo–p–dioxin–like Chemicals", *Environmental Toxicoloy*, vol. 13, No. 10, (1994) pp. 1581–1588.

Postlind et al., "Response of Human CYP1–Luciferase Plasmids to 2,3,7,8–Tetrachlorodibenzo–p–dioxin and Polycyclic Aromatic Hydrocarbons", *Toxicology and Applied Pharmacology*, vol. 118, (1993) pp. 255–262.

Anderson et al., "A Biomarker, P450 RGS, for Assessing the Induction of Environmental Samples", *Environmental Toxicology and Chemistry*, vol. 14, No. 7, (1995) pp. 1159–1169.

Albro et al., "Methods for the Quantitative Determination of Multiple, Specific Polychlorinated Dibenzo–p–dioxin and Dibenzofuran Isomers in Human Adipose Tissue in the Parts–per–Trillion Range. An Interlaboratory Study", *Anal. Chem.*, vol. 57, No. 13, (1985) pp. 2717–2725.

Okino et al., "2,3,7,8–Tetrachlorodibenzo–p–dioxin Induces the Nuclear Translocation of Two XRE Binding Proteins in Mice", *Pharmacogenetics*, vol. 3, (1993) pp. 101–109.

Phillips et al., "Chlorinated Hydrocarbon Levels in Human Serum: Effects of Fasting and Feeding", *Arch. Environ. Contam. Toxicol.*, vol. 18, (1989) pp. 495–500.

Yao et al., "DNA Sequence Determinants for Binding of Transformed Ah Receptor to a Dioxin–Responsive Enhancer", *Biochemistry*, vol. 31, No. 21, (1992) pp. 5060–5067.

Denison et al., "Inducible, Receptor–Dependent Protein–DNA Interactions at a Dioxin–Responsive Transcriptional Enhancer", *Proc. Natl. Acad. Sci. USA*, vol. 85, (1988) pp. 2528–2532.

Denison et al., "Xenobiotic–Inducible Transcription of Cytochrome P450 Genes", *The Journal of Biological Chemistry*, vol. 270, No. 31, (1995) pp. 18175–18178.

Helferich et al., "Ultraviolet Photoproducts of Tryptophan Can Act as Dioxin Agonists", *Molecular Pharmacology*, vol. 40, (1991) pp 674–678.

Richter et al., "Development of an in vitro Rainbow Trout Cell Bioassay for AhR–mediated Toxins", *Organohalogen Compounds*, vol. 21, (1994) pp. 213–216.

Ahlborg et al., "Toxic Equivalency Factors for Dioxin–line PCBs", *Chemosphere*, vol. 28, No. 6, (1994) pp. 1049–1063.

Safe, "Comparative Toxicology and Mechanism of Action of Polychlorinated Dibenzo–p–dioxins and Dibenzofurans", *Ann. Rev. Pharmacol. Toxicol.*, vol. 26, (1986) pp. 371–399.

Casterline et al., "Screening of Fresh Water Fish Extracts for Enzyme–Inducing Substances by an Aryl Hydrocarbon Hydroxylase Induction Bioassay Technique", *J. Assoc. Off. Anal. Chem.*, vol. 66, No. 5, (1983) pp. 1136–1139.

Fujisawa–Sehara et al., "Characterization of Xenobiotic Responsive Elements Upstream from Drug–Metabolizing Cytochrome P–450c Gene: A Similarity to Glucocorticoid Regulatory Elements", *Nucleic Acids Research*, vol. 15, No. 10, (1987) pp. 4179–4191.

Rappe et al., "Chemical Properties and Analytical Methods", Chp. 2 of *Halogenated Biphenyls, Terphenyls, Naphthalenes, Dibenzodioxins, and Related Products*, published by Elsevier/North–Holland Biomedical Press, (1980) pp. 41–59.

Whitlock, "The Regulation of Cytochrome P–450 Gene Expression", *Ann. Rev. Pharmacol. Toxicol.*, vol. 26, (1986) pp. 333–365.

Thompson et al., "Modulation of Firefly Luciferase Stability and Impact on Studies of Gene Regulation", *Gene*, vol. 103, (1991) pp. 171–177.

Lusska et al., "Protein–DNA Interactions at a Dioxin–responsive Enhancer", *The Journal of Biological Chemistry*, vol. 268, No. 9, (1993) pp. 6575–6580.

Denison et al., "Structure and Function of the Ah Receptor for 2,3,7,8–Tetrachlorodibenzo–p–dioxin", *The Journal of Biological Chemistry*, vol. 261, No. 9, (Mar. 1986) pp. 3987–3995.

Bank et al., "Species–Specific Binding of Transformed Ah Receptor to a Dioxin Responsive Transcriptional Enhancer", *European Journal of Pharmacology, Environmental Toxicology and Pharmacology Section*, vol. 228, (1992) pp. 85–94.

Safe et al., "Polychlorinated Dibenzo–p–dioxins and Dibenzofurans: Correlation Between in vitro and in vivo Structure–activity Relationships (SARs)", *Chemosphere*, vol. 15, Nos. 9–12, (1986) pp. 1725–1731.

Miller et al., "Biochemical and Genetic Analysis of Variant Mouse Hepatoma Cells Defective in the Induction of Benzo(a)pyrene–metabolizing Enzyme Activity", *The Journal of Biological Chemistry*, vol. 258, No. 6, (1983) pp. 3523–3527.

Whitlock, "Mechanistic Aspects of Dioxin Action", *Chem. Res. Toxicol.*, vol. 6, No. 6, (1993) pp. 754–763.

Fisher et al., "Organization and Function of a Dioxin–responsive Enhancer", *The Journal of Biological Chemistry*, vol. 265, No. 17, (Jun. 1990) pp. 9676–9681.

Sawyer et al., "Comparative Aryl Hydrocarbon Hydroxylase Induction Activities of Commercial PCBs in Wistar Rats and Rat Hepatoma H–4–II E Cells in Culture", *Chemosphere*, vol. 13, No. 7, (1984) pp. 695–701.

Tillit et al., "Characterization of the H4IIE Rat Hepatoma Cell Bioassay as a Tool for Assessing Toxic Potency of Planar Halogenated Hydrocarbons in Environmental Samples", *Environ. Sci. Technol.*, vol. 25, No. 1., (1991) pp. 87–92.

Van den Berg et al., "The Toxicokinetics and Metabolism of Polychlorinated Dibenzo–p–dioxins (PCDDs) and Dibenzofurans (PCDFs) and Their Relevance for Toxicity", *Critical Reviews in Toxicology*, vol. 24, No. 1, (1994) p. 1 of pp. 1–74.

Tillitt et al., "H4IIE Rat Hepatoma Cell Bioassay–Derived 2,3,7,8–Tetrachlorodibenzo–p–dioxin Equivalents in Colonial Fish–Eating Waterbird Eggs from the Great Lakes", *Arch. Environ. Contam. Toxicol.*, vol. 21, (1991) pp. 91–101.

Webster et al., "Overview The Dioxin Debate", *Dioxins and Health*, (1994) Chp. 1, pp. 1–6.

DeVito et al., Toxicology of Dioxins and Related Chemicals, *Dioxins and Health*, (1994) Chp. 5, pp. 139–149.

Henry et al., "Transformation of the Aryl Hydrocarbon Receptor to a DNA–binding Form is Accompanied by Release fo the 90 kDa Heat–shock Protein and Increased Affinity for 2,3,7,8–Tetrachlorodibenzo–p–dioxin", *Biochem. J.*, vol. 294, (1993) pp. 95–101.

Denison et al., "Identification of the Ah Receptor in Selected Mammalian Species and Induction of Aryl Hydrocarbon Hydroxylase", *Eur. J. Biochem.*, vol. 147, (1985) pp. 429–435.

Goldstein et al., "Mechanism of Action and Structure–activity Relationships for the Chlorinated Dibenzo–p–dioxins and Related Compounds", *Halogenated Biphenyls, Terphenyls, Naphthalenes, Dibenzodioxins and Related Compounds*, (1989) Chp. 9, pp. 239–243.

Virta et al., "A Luminescence–Based Mercury Biosensor", *Analytical Chemistry*, vol. 67, No. 3, (Feb., 1995) pp. 667–669.

Hankinson, "The Aryl Hydrocarbon Receptor Complex", *Annu. Rev. Pharmacol. Toxicol.*, vol. 35, (1995) pp. 307–340.

Poland et al., "2,3,7,8–Tetrachlorodibenzo–p–dioxin and Related Halogenated Aromatic Hydrocarbons: Examination of the Mechanism of Toxicity", *Ann. Rev. Pharmacol. Toxicol.*, vol. 22, (1982) pp. 517–553.

Denison et al., "Species Variation in Ah Receptor Transformation and DNA Binding", *Banbury Report 35: Biological Basis for Risk Assessment of Dioxins and Related Compounds*, (1991) pp. 337–350.

Safe, "Polychlorinated Biphenyls (PCBs): Environmental Impact, Biochemical and Toxic Responses, and Implications for Risk Assessment", *Critical Reviews in Toxicology*, vol. 24, No. 2, (1994) pp. 87–149.

Fisher et al., "Activation of Transcription as a General Mechanism of 2,3,7,8–Tetrachlorodibenzo–p–dioxin Action", *Molecular Carcinogenesis*, vol. 1, (1989) pp. 216–221.

Giesy et al., "Dioxins, Dibenzofurans, PCBs and colonial, Fish–Eating Water Birds", *Dioxins and Health*, (1994) Chp. 9, pp. 249–307.

Bradford,"A Rapid and Sensitive Methof for the Quantitation of Microgram Quantities of Protein Utilizing the Principle of Protein–Dye Binding", *Analytical Biochemistry*, vol. 72, (1976) pp. 248–254.

Karin et al., "Characterization of DNA Sequences through which Cadmium and Glucocorticoid Hormones Induce Human Metallothionein–II$_A$gene", *Nature*, vol. 308, (1984) pp. 513–519.

Safe, "Polychlorinated biphenyl (PCBs), Dibenzo–p–dioxins (PCDDs), Dibenzofurans (PCDFs), and Related Compounds: Environmental andMEchanistic Considerations which Support the Development of Toxic Equivalency Factors (TEFs)", *Critical Reviews in Toxicology*, vol. 21, Issue 1, (1990) pp. 51–88.

Pollenz et al., "The Aryl Hydrocarbon Receptor and Aryl Hydrocarbon Receptor Nuclear Translocator Protein Show Distinct Subcellular Localizations in Hepa 1c1c7 Cells by Immunofluorescence Microscopy", *Molecular Pharmacology*, vol. 45, (1993) pp. 428–0438.

Denison et al., "Application of the CALUX Bioassay System for the detectionof Dioxin–like Chemicals (Ah Receptor Ligands) in Whole Serum Samples and In Extracts from Commercial and Consumer Products", *Organohalogen Compounds*, vol. 27, (1996) pp. 280–284.

Aarts et al., "Application of the Chemical–activated Luciferase Expression (CALUX) Bioassay for Quantification of Dioxin–like Compounds in Small Samples of Human Milk and Blood Plasma", *Organohalogen Compounds*, vol. 27, (1996) pp. 285–290.

Murk et al., "Application of the CALUX (Chemical Activated Luciferase Gene Expression) Assay for Measuring TCDD–equivalents in Sediment, Pore Water and Blood Plasma Samples", *Organohalogen Compounds*, vol. 27, (1996) pp. 291–296.

Bovee et al., "Biological Screening of Ah Receptor Agonist Activity in Butter fat and Coconut Oil by Means of Chemical–activated Luciferase Expression in a Genetically Engineered Cell Line (CALUX)", *Organohalogen Compounds*, vol. 27, (1996) pp. 303–308.

Legler et al., "Determination of Dioxin–and Estrogene–like Activity in Sediment Extracts Using in vitro CALUX Assays", *Organohalogen Compounds*, vol. 29, (1996) pp. 347–352.

BIOASSAY FOR DETECTING 2,3,7,8-TETRACHLORODIBENZO-PARA-DIOXIN AND TCDD-LIKE COMPOUNDS AND NOVEL RECOMBINANT CELL LINE USEFUL THEREFOR

GOVERNMENT INTEREST

The U.S. Government has rights to this invention pursuant to Contract No. ES-04699 between the Department of Health & Human Services/National Institutes of Health and the University of California.

TECHNICAL FIELD

This invention relates, in general, to a bioassay method for the detection of certain toxins and to novel recombinant cell lines useful in the detection method. More particularly, the present invention relates to a novel bioassay system for testing for polychlorinated di-aromatic hydrocarbons, where the bioassay system is made by inserting dioxin responsive elements in front of a luciferase reporter gene, and then, transfecting the resultant recombinant expression plasmid into mouse hepatoma cells.

ABBREVIATIONS

It is noted that the following abbreviations are employed for convenience throughout this specification.

| abbreviations | definitions |
| --- | --- |
| PAH | polyaromatic hydrocarbon (certain PAHs are toxins) |
| BA | benz[a]anthracene, a kind of PAH |
| BNF | β-naphthoflavone, a kind of PAH |
| 3-MC | 3-methylcholanthrene, a kind of PAH |
| PCDH | polychlorinated di-aromatic hydrocarbon (these are toxins that produce tumors, birth defects, etc.), a kind of PAH |
| PCB | polychlorinated biphenyl, a kind of PCDH |
| AROCLOR 1242 | trade name of a mixture of PCBs with an average 42% chlorination |
| AROCLOR 1254 | trade name of a mixture of PCBs with an average 54% chlorination |
| AROCLOR 1260 | trade name of a mixture of PCBs with an average 60% chlorination |
| 3,3',4,4'-TCB | 3,3',4,4'-tetrachlorobiphenyl, a kind of PCB |
| 3,3',4,4',5-PCB | 3,3',4,4',5-pentachlorobiphenyl, a kind of PCB |
| 2,3,4,4',5-PCB | 2,3,4,4',5-pentachlorobiphenyl, a kind of PCB |
| 2,3,3',4,4',5-HCB | 2,3,3',4,4',5-hexachlorobiphenyl, a kind of PCB |
| 2,2',5,5'-TCB | 2,2',5,5'-tetrachlorobiphenyl, a kind of PCB |
| PCDF | polychlorinated dibenzofuran, a kind of PCDH |
| 2,3,7,8-TCDF | 2,3,7,8-tetrachlorodibenzofuran, a kind of PCDF |
| 2,3,4,7,8-PCDF | 2,3,4,7,8-pentachlorodibenzofuran, a kind of PCDF |
| PCDD | polychlorinated dibenzo-p-dioxin, a kind of PCDH |
| TCDD | 2,3,7,8-tetrachlorodibenzo-p-dioxin, a kind of PCDD |
| 1,2,4,7,8-PCDD | 1,2,4,7,8-pentachlorodibenzo-p-dioxin, a kind of PCDD |
| DRE | dioxin responsive element, a sequence found in the promoter region of a gene which confers TCDD responsiveness on the gene |
| AhR | aryl hydrocarbon receptor, a soluble intracellular protein receptor to which PCDHs bind with high affinity, and the PCDH bound AhR complex binds to DREs and causes changes in expression of the associated gene |
| Luc | luciferase, an enzyme from fireflies |
| EROD | 7-ethoxyresorufin-O-deethylase enzyme |
| arnt | Ah receptor nuclear translocator protein |
| AHH | aryl hydrocarbon hydroxylase enzyme |
| pM | pico molar, $1 \times 10^{-12}$ molar |
| nM | nano molar, $1 \times 10^{-9}$ molar |
| PAP or pap | placental alkaline phosphatase enzyme |
| DMSO | dimethyl sulfoxide |
| MMTV | mouse mammary tumor virus |
| MDL | minimal detection level |
| RLU | relative light unit |
| PBS | phosphate buffered saline |
| G418 | trade name of an antibiotic from Gibco |
| Gud | good |
| ED50 | toxic equivalent factors for PCDHs measured by their ability to induce EROD/AHH activity in cell cultures |
| pSV2neo | simian virus promotor that drives expression of a gene that confers resistance to the antibiotic, neomycin |
| SV40 | simian virus 40 |
| LTR | long terminal repeat |
| TCDD-like compounds | PAHs that are not dioxins but that will cause the novel mouse H1L1.1 cell line (described below) to respond with luminescence in a way like TCDD causes the novel mouse H1L1.1 cell line to respond with luminescence, and examples include TCDD-like fused-ring polyaromatic hydrocarbon compounds, TCDD-like polychlorinated di-aromatic hydrocarbon compounds, and combinations thereof |

BACKGROUND OF THE INVENTION

Compounds of the polychlorinated di-aromatic hydrocarbon group are toxic pollutants that are harmful to humans. Some PCDHs are contaminants of herbicides, such as Agent Orange, whereas others are generated from various chemical processes, such as the incineration of chlorinated polymeric plastics or of polychlorinated biphenyls. Health hazards to humans and animals from PCDHs include a variety of species and tissue specific effects, such as tumor promotion, birth defects, hepatotoxicity, immunotoxicity, dermal toxicity, alterations in endocrine homeostasis, and induction of numerous enzymes including that of cytochrome P4501A1.

Gas chromatography techniques and mass spectrometry techniques for the detection and quantitative analysis of PCDHs are costly and time-consuming, which has led to the development of various bioassays. The following journal articles and patents are of interest in connection with bioassays for PCDHs.

El-Fouly et al., "Production of a Novel Recombinant Cell Line for Use as a Bioassay system for Detection of 2,3,7, 8-Tetrachlorodibenzo-p-dioxin-like Chemicals", Vol. 13, No. 10, *Environmental Toxicology and Chemistry*, pp. 1581–1588 (1994) show a bioassay made by binding AhR recognition sites on a human PAP vector, and transfecting the resultant into mouse hepatoma cells. However, use of the PAP enzyme in a reporter gene is known to have the drawback that many cells, particularly human epithelial cells, contain endogenous levels of heat-stable PAP activity that interferes with the bioassay analysis.

Postlind et al., "Response of Human CYP1-Luciferase Plasmids to 2,3,7,8-Tetrachlorodibenzo-p-dioxin and Polycyclic Aromatic Hydrocarbons", Vol. 118, *Toxicology and Applied Pharmacology*, pp. 255–268 (1993) describe a bioassay made by binding the 5'-flanking region of human CYP1A1 into a luciferase vector, and the resultant is transfected into human hepatoma cells. The particular cell line is also known as 101L. Postlind et al. tested four PCDHS, namely TCDD, 3-methylcholanthrene, benz[a]anthracene, and benzo[a]pyrene. As discussed in more detail below, toxicity testing with 101L has shown it to be sensitive only down to a minimal detection level of 1 part per million of TCDD per sample, which is 1,000,000,000 parts per quadrillion.

Anderson et al., "A Biomarker, P450 RGS, for Assessing the Induction Potential of Environmental Samples", Vol. 14, no. 7, *Environmental Toxicology and Chemistry*, pp. 1159–1169 (1995) use the same 101L cell line as Postlind et al. use to test various PCDHs, including TCDD. A sensitivity of TCDD per sample of 0.05 ng/g, which is 50,000 parts per quadrillion, is reported (bottom of Table 10, p. 1167).

Kennedy et al., "Ethoxyresorufin-O-deethylase and Porphyrn Analysis in Chicken Embryo Hepatocyte Cultures with a Fluorescence Multiwell Plate Reader", Vol. 211, *Analytical Biochemistry*, pp. 102–112 (1993) show a bioassay using the EROD enzyme transfected into chicken embryo hepatocyte cultures. For detecting 3,3',4,4'-tetrachlorobiphenyl, Kennedy et al. disclose a sensitivity of 10 parts per trillion, which is 10,000 parts per quadrillion.

U.S. Pat. No. 4,238,472 to Albro et al. shows a radioimmunoassay for dioxins (including TCDD) in the parts per trillion range, which is 1,000 parts per quadrillion. The immunoassay uses a polyclonal antibody derived from 1-amino-3,7,8-trichlorodibenzo-p-dioxin.

Each of U.S. Pat. No. 4,798,807 to Vanderlaan et al. and U.S. Pat. No. 5,429,925 to Vanderlaan et al. describes the production of monoclonal antibodies directed against PCDHs using hybridomas produced by fusion of SP2/0 mouse myeloma cells with spleenocytes obtained from immunized BALB/c and Biozzi mice. The monoclonal antibodies are used in an immunoassay to detect halogenated dioxins and dibenzofurans in industrial samples containing these PCDHs and show a sensitivity of a few parts per trillion, which is a few 1,000 parts per quadrillion. A drawback is that the bioassay cross-reacts with a large number of dioxins that have no toxicological activity and is not particularly specific for TCDD.

U.S. Pat. No. 4,865,972 to Hunter describes conducting immunoprecipitation on an aliquot of a sample contaminated with various PCDHs (including TCDD), and then, conducting a bioassay using the treated sample. A bioassay is also conducted on an aliquot of that has not undergone the immunoprecipitation procedure. The results of the two bioassays are then compared to determine an indirect measure of the amount of TCDD.

U.S. Pat. No. 5,128,244 to Poland et al. describes a bioassay for recognizing the presence of dioxins in a sample. The bioassay uses the mouse AhR and a halogenated dioxin that is radioactively labeled with $^{125}$I. PCDHs in the test sample compete with the $^{25}$I-labeled dioxin for binding to the mouse AhR. The amount of competition observed serves as a measure of the amount of PCDHs in the test sample.

U.S. Pat. No. 5,378,822 to Bradfield et al. suggests the use of expressed proteins from the cDNA for mouse AhR or human AhR in a bioassay to detect PCDHs in samples.

SUMMARY AND OBJECTS OF THE INVENTION

Therefore, the present invention provides a novel recombinant cell line deposited at the American Type Culture Collection under ATCC accession number CRL-12286 and also known as the mouse H1L1.1 cell line (or colloquially as the mouse H1L1.1c2 cell line), which will respond to certain polyaromatic hydrocarbons with expression (i.e., luminescence) of luciferase. Preferably, the polyaromatic hydrocarbons include polychlorinated dibenzo-para-dioxins (such as 2,3,7,8-tetrachlorodibenzo-para-dioxin) and TCDD-like compounds (such as TCDD-like fused-ring polyaromatic hydrocarbon compounds and TCDD-like polychlorinated di-aromatic hydrocarbon compounds). Also, preferably, the TCDD-like polychlorinated di-aromatic hydrocarbon compounds include compounds such as polychlorinated dibenzofurans and coplanar polychlorinated biphenyls.

More particularly, the novel mouse H1L1.1 cell line comprises a mouse hepatoma cell line that is stably transfected with a recombinant expression plasmid, wherein the recombinant expression plasmid comprises dioxin responsive elements inserted upstream of a luciferase gene.

Also, the present invention provides a method for the quantitative analysis of these certain polyaromatic hydrocarbons in samples. The method comprises the steps of: (a) providing a sample suspected of containing at least one of these polyaromatic hydrocarbons and (b) determining the amount of the polyaromatic hydrocarbon in the sample by a bioassay procedure using a recombinant cell line deposited at the American Type Culture Collection under ATCC accession number CRL-12286 and also known as the mouse H1L1.1 cell line. Preferably, in step (b), the sample containing the polyaromatic hydrocarbon is solubilized in a solvent, for use with the cell line. Examples of suitable solvents are dimethyl sulfoxide and fetal calf serum.

In one embodiment of the method using the polyaromatichydrocarbon, 2,3,7,8-tetrachlorodibenzo-para-dioxin, the bioassay was able to detect as little as about 100 parts of this dioxin per quadrillion parts of sample.

Thus, it is an object of the invention to provide a recombinant cell line and an immunoassay method that specifically detects 2,3,7,8-tetrachlorodibenzo-para-dioxin.

Furthermore, it is an advantage of the recombinant cell line and the immunoassay method that polyaromatic hydrocarbon compounds can be detected in extremely small amounts, i.e., at a minimum detection level as low as 100 parts per quadrillion for 2,3,7,8-tetrachlorodibenzo-para-dioxin.

Some of the objects and advantages of the invention having been stated, other objects will become evident as the description proceeds, in connection with the Figures and Examples described below.

DETAILED DESCRIPTION OF THE INVENTION

As noted, the present invention involves a reporter gene-linked bioassay procedure. The procedure allows for the analysis of samples in order to determine quantitatively the presence of certain particular polyaromatic hydrocarbons, especially polychlorinated di-aromatic hydrocarbons, more especially TCDD, using a unique cell line. The cell line has been placed in the public depository of the American Type Culture Collection 10801 University Boulevard, Manassas, Va. 20110-2209, and is identified with accession number CRL-12286, and is also known as the mouse H1L1.1 cell line. The deposited material has been deposited under the terms of the Budapest Treaty on Feb. 18, 1997. All restrictions on the availablity to the public of the deposited material will be irrevocably removed upon the granting of a patent. All restrictions on the availability to the public of the deposited material will be irrevocably removed upon the granting of a patent.

The novel mouse H1L1.1 cell line comprises a recombinant expression plasmid stably transfected into mouse hepatoma cells. The plasmid contains dioxin responsive elements inserted upstream of the gene for luciferase. The novel mouse H1L1.1 cell line responds to the particular polyaromatic hydrocarbons with expression of luciferase (measured by luminescence).

The particular polyaromatic hydrocarbon compounds for which the novel mouse H1L1.1 cell line can be employed for testing include polychlorinated dibenzo-para-dioxins (such as 2,3,7,8-tetrachlorodibenzo-para-dioxin, which is the most potent of the PCDHs that are toxic), various TCDD-like compounds, and combinations thereof.

More particularly, the TCDD-like fused-ring polyaromatic compounds include, but are not limited to, benz [a] anthracene, β-naphthoflavone, 3-methylcholanthrene, and combinations thereof. Also, more particularly, the TCDD-like polychlorinated di-aromatic hydrocarbon compounds include, but are not limited to, polychlorinated dibenzofurans, coplanar polychlorinated biphenyls, and combinations thereof. Examples of polychlorinated dibenzofurans detected by the bioassay are 2,3,4,7,8-pentachlorodibenzofuran and 2,3,7,8-tetrachlorodibenzofuran. Coplanar polychlorinated biphenyls detected by the bioassay include, but are not limited to, 3,3',4,4'-tetrachlorobiphenyl, 3,3',4,4',5-pentachlorobiphenyl, 2,3,4,4',5-pentachlorobiphenyl, and 2,3,3',4,4',5-hexachlorobiphenyl.

It is noted that 2,2',5,5'-tetrachlorobiphenyl is not coplanar, and thus, is not a TCDD-like compound as defined above. Moreover, as described further below, 2,2',5,5'-TCB will not cause the novel mouse H1L1.1 cell line to respond with luminescence and acts as an antagonist to the novel mouse H1L1.1 cell line when added with TCDD.

The bioassay particularly demonstrates a high affinity and selectivity toward certain PAHs, particularly 2,3,7,8-tetrachlorodibenzo-para-dioxin. Moreover, the bioassay allows for the determination of the presence of TCDD in test samples at a minimum detection level of about 100 parts per quadrillion. Typically, the bioassay for TCDD and the above-noted TCDD-like compounds can be performed in about 8 hours or less, more preferably about 6 hours or less, even more preferably about 4 hours or less, rather than days as with prior art gas chromatograph/mass spectrometry assays.

The bioassay method involves providing a sample suspected of containing at least one of these particular PAHs and determining the amount of the PAH in the sample by a bioassay procedure using the recombinant cell line deposited at the American Type Culture Collection under ATCC accession number CRL-12286 and also known as the mouse H1L1.1 cell line. Preferably, the PAHs from the sample are administered to the H1L1.1 solubilized in a suitable solvent. Suitable solvents are those that will dissolve the PAH, but not be toxic to the cell line, i.e., will not kill the cell line. Examples of suitable solvents are dimethyl sulfoxide and fetal calf serum.

Discussion of Figures and Laboratory Examples

The following are the sources of the materials employed in the Laboratory Examples described below.

Molecular biological enzymes were purchased from New England Biolabs (Beverly, Mass.) or Bethesda Research Laboratory (Gaithersburg, Md.). Polybrene, BA, BNF, and 3-MC were from Aldrich Chemical Co. (Milwaukee, Wis.). The antibiotic G418 was from Gibco/BRL (Grand Island, N.Y.). The chemicals 2,3,7,8-TCDD, 2,3,7,8-TCDF, 2,3,4, 7,8-PCDF, 1,2,4,7,8-PCDD, 3,3',4,4'-TCB, 3,3',4,4',5-PCB, 2,3,4,4',5-PCB, 2,3,3',4,4',5-HCB, AROCLOR 1242, AROCLOR 1254, and AROCLOR 1260 were obtained from Dr. Stephen H. Safe (Texas A&M University, College Station, Tex.). The chemical 2,2',5,5'-TCB was purchased from Accustandards, Inc. (New Haven, Conn.). These compounds are extremely toxic substances and were handled with special precautions, including the use of disposable bench top paper, gloves, plastic ware, and glassware.

Figure 1:
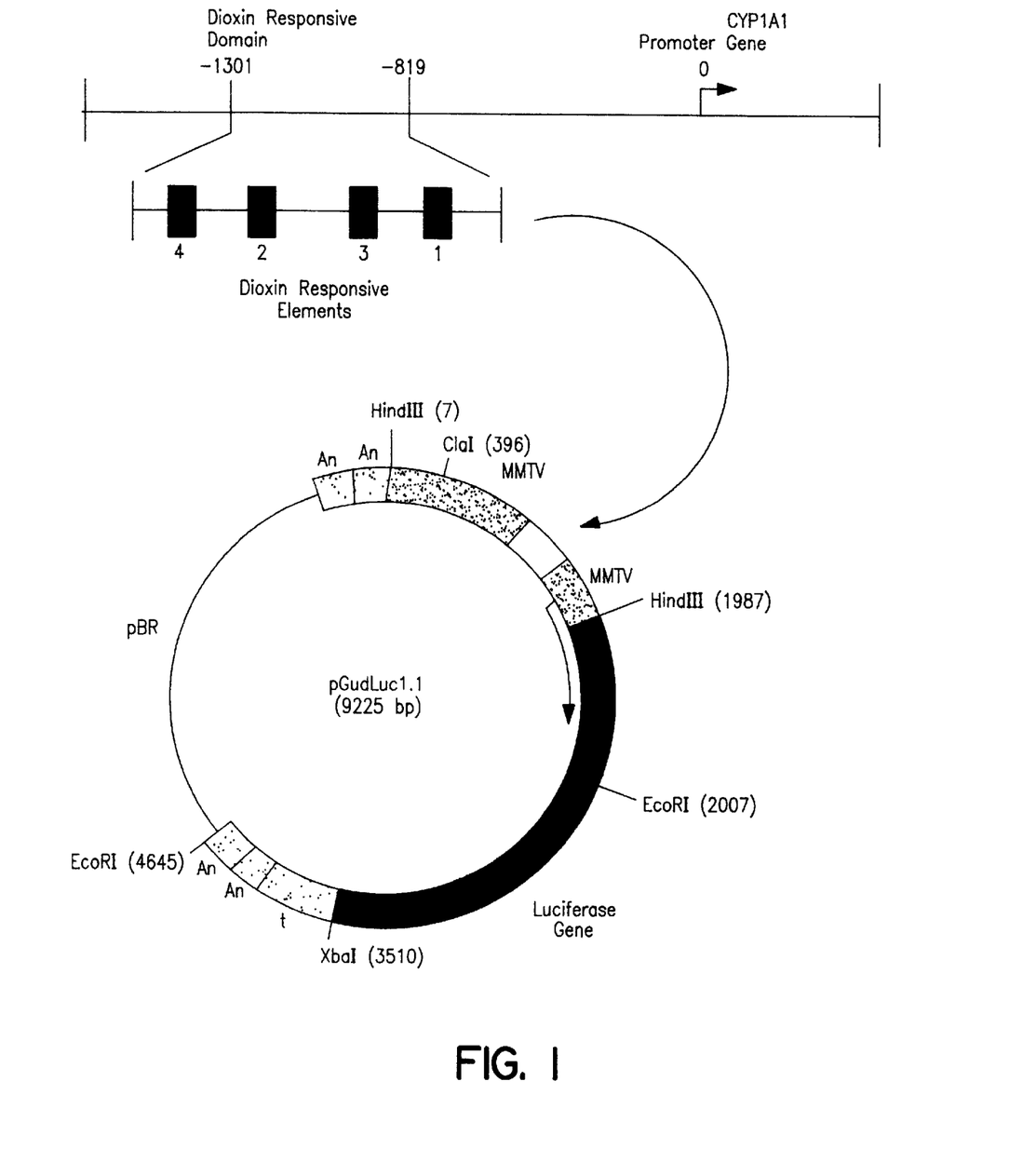
FIG. 1 is a schematic showing the structure of the luciferase expression vector, pGudLuc1.1.

As can be seen with reference to FIG. 1, depicted is a schematic showing the structure of the expression vector, pGudLuc1.1. The vector contains the firefly luciferase gene (filled black in the graph) under control of the MMTV LTR (hatched) viral promoter. Also, the vector contains a 484-bp fragment from the upstream region of the CYP1A1 gene. The fragment contains four DREs (unfilled in the graph) present directly upstream of the MMTV viral promoter and confers PCDH responsiveness upon the viral promoter and luciferase gene. The pBR322 portion of the plasmid is denoted by a line. The transcription start site is denoted by an arrow. An and t (speckled in the graph) indicate the position of poly(A) terminator signals and the SV40 small t antigen intron, respectively.

In general, the expression vectors pGudLuc1.0 and pGudLuc1.1 were prepared as follows. A 1330-bp HindIII fragment or an 1810-bp HindIII fragment isolated from the plasmid, pMpap1.0 or pMpap1.1, respectively (see, El-Fouly et al., supra), was subcloned into the HindIII site immediately upstream of the luciferase gene in the plasmid pGL2-basic (purchased from Promega).

As can be seen in FIG. 1, the 1330-bp fragment contains a portion of the MMTV long terminal repeat, inclusive of the viral promoter, but lacking functional glucocorticoid responsive enhancers. On the other hand, the 1810-bp fragment contains the 1330-bp MMTV fragment as well as a 484-bp fragment isolated from the 5'-flanking region of the mouse cytochrome P4501A1 gene. The 484-bp fragment contains four DREs which confer PCDH responsiveness upon the MMTV viral promoter, and thus, expression (i.e., luminescence) of the luciferase reporter enzyme can be induced by PCDHs. Recombinants were isolated as ampicillin-resistant colonies in *Escherichia coli* DH5 and the orientation of the insert was confirmed by restriction enzyme analysis.

Since previous studies as reported by Denison et al. in "Inducible, Receptor-Dependent Protein-DNA Interactions at a Dioxin-Responsive Transcriptional Enhancer", *Proc. Natl. Acad. Sci. USA*, Vol. 85, pp. 2528–2532 (1988) demonstrated that transfected DRE sequences can confer PCDH responsiveness upon a heterologous promoter and gene, transient transfection of the reporter constructs pGudLuc1.0 (which lacks DREs) and pGudLuc1.1 (which contains DREs) into a variety of cell lines was performed, as reported in Table 1.

More specifically, the following cells were obtained from the source indicated. Wild-type and AhR-defective (BPRc1 and TAO, respectively) mouse hepatoma (Hepa1c1c7) cells (Hepa1), derived from a C57B1 mouse liver tumor, were obtained from J. P. Whitlock, Jr. (Stanford University). These cells were grown as previously described by Miller et al. in "Biochemical and Genetic Analysis of Variant Mouse Hepatoma Cells Defective in the Induction of Benzo(a) pyrene Metabolizing Enzyme Activity", *J. Biol. Chem.*, Vol. 258, pp. 3523–3527 (1983). Additionally, mouse hepatoma (MLE/BV) cells, derived from a spontaneously immortalized C3H/HeN mouse liver cell, were obtained from B. V. Madhukar (Indiana University School of Medicine, Indianapolis, Ind.) and were grown as described for the Hepa1 cells. Rat hepatoma (H4IIe) cells, guinea pig intestinal adenocarcinoma (GPC16) cells, hamster lung (AHL) cells, human hepatoma (HepG2) cells, human breast tumor (MCF7) cells, and human intestinal epithelial (LS180) cells were obtained from the American Type Culture Collection (Rockville, Md.). Until transfection, all of the cells were maintained according to their respective cell-type-specific culture protocols.

Transfection was accomplished as follows. Using polybrene as previously described by Helferich et al. in "Photooxidized Products of Tryptophan Can Act as Dioxin Agonists", *Mol. Pharmacol.*, Vol. 40, pp. 674–678 (1991), plates of cells (approximately 80% confluent) were transiently transfected with the desired plasmid (15 μg). Then, the transfected cells were allowed to grow for 48 hours, followed by the addition of either DMSO (1 μl/ml) or TCDD (1 nM) solubilized in DMSO, which was followed by incubation for 24 hours. Next, the plates were transferred onto ice, and the media were removed, after which the plates were rinsed twice with cold PBS. Then, 200 μl of luciferase lysis buffer (purchased from Promega) was used to lyse the cells. The lysed cell samples were collected and transferred into a microfuge tube. Cell debris was pelleted by centrifugation, and the supernatants were collected. The supernatant samples were assayed for TCDD-inducible luciferase activity in the following manner.

Using the stabilized luciferase assay system (purchased from Promega), luciferase activity in an aliquot of the cleared lysed cell supernatant (20 μl) was determined by mixing it with 100 μl of luciferase assay reagent (purchased from Promega) and measuring the resulting luminescence in a Turner Luminometer or Dynatech ML3000 microplate luminometer (light output was integrated over 1 minute after a delay time of 30 seconds). The lysates exhibited a stable luciferase activity at room temperature for at least 1.5 hours.

Using a microplate adaptation of the method reported by Bradford in "A Rapid Sensitive Method for the Quantitation of Microgram Quantities of Protein Utilizing the Principle of Protein-Dye Binding", *Anal. Biochem.*, Vol. 172, pp. 248–254 (1976), luciferase activity was standardized to the protein concentration of the supernatant (with bovine serum albumin as the protein standard). Because of instrument differences in luminescence measurement and data output, luciferase activity was determined as relative light units (RLU) per microgram of protein, which was converted to milligram of protein as reported in the Tables below.

TABLE 1

TCDD-Inducible Luciferase Activity in Several Cell Lines Transiently Transfected with the Expression Vectors, pGudLuc1.0 and pGudLuc1.1

| Cell line | Vector | Luciferase activity (RLU/mg protein)* | | Fold induction |
|---|---|---|---|---|
| | | DMSO | TCDD in DMSO | |
| Mouse | | | | |
| Hepa1c1c7** | Luc1.0 | 0.1 | 0.1 | 1.0 |
| Hepa1c1c7** | Luc1.1 | 0.2 | 12.1 | 60.5 |
| Hepa1-BPRc1 | Luc1.1 | 0.5 | 0.8 | 1.6 |
| Hepa1-TAO | Luc1.1 | 0.4 | 1.8 | 4.5 |
| MLE-BV | Luc1.1 | 0.2 | 13.2 | 66.0 |
| Human | | | | |
| HepG2 | Luc1.1 | 10.4 | 690 | 66.3 |
| MCF7 | Luc1.1 | 1.9 | 63.5 | 33.4 |
| LS180 | Luc1.1 | 1.4 | 26.0 | 18.6 |
| Rat H4IIE | Luc1.1 | 1.2 | 34.2 | 28.5 |
| Guinea pig GPC16 | Luc1.1 | 3.8 | 28.8 | 7.6 |
| Hamster AHL | Luc1.1 | 30 | 174 | 5.8 |

*Values are the mean of triplicate transfections.
**Wild type.

As can be seen from Table 1, TCDD-treatment of wild type Hepa1c1c7 cells transiently transfected with pGudLuc1.0 (which lacks DREs) failed to induce luciferase activity. On the other hand, wild type Hepa1c1c7 cells transfected with pGudLuc1.1 (which contains DREs) significantly induced luciferase activity (60-fold). These results demonstrate the induction response has both a TCDD-dependent nature and DRE-dependent nature. In addition, the failure of TCDD treatment to induce luciferase activity in pGudLuc1.1-transfected variant Hepa1-BPRc1 cells (which contain a defective arnt protein and are not inducible) and the reduced inducibility in the variant Hepa1-TAO cells (which contain reduced levels of AhR) demonstrates that induction of luciferase activity is also AhR-dependent. These results are consistent with previous transfection studies in cell lines (see, Denison et al., supra, and El-Fouly et al., supra).

Thus, these results indicate that the AhR present in a variety of species and tissues can functionally interact with the mouse DREs present in the expression vector, pGudLuc1.1. In addition, the results demonstrate the utility of this expression vector for the generation of inducible, species-specific recombinant bioassay systems to detect TCDD and TCDD-like compounds and to examine species differences in TCDD responsiveness.

As further can be seen from Table 1, AhR-containing continuous cell lines from a variety of species and tissues (mouse liver, rat liver, human liver, guinea pig intestinal epithelia, human intestinal epithelia, hamster lung, and human breast) showed TCDD-dependent induction of luciferase activity. Therefore, since it was observed that a variety of cells transiently transfected with pGudLuc1.1 can respond to TCDD with the induction of luciferase activity, five stable cell lines (Hepa1, MLE/BV, H4IIE, GPC16, and HepG2) were chosen to be stably transfected with the pGudLuc1.1 plasmid.

Cells from each of these five stable cell lines were cotransfected with the vectors, pGudLuc1.1 and pSV2neo (15 µg of each). Following a 24 hour incubation, the cotransfected cells were split 1 to 10 and replated into a selective medium containing the antibiotic, G418. After 2–3 weeks of growth, individual cell colonies were identified and isolated. Although numerous inducible cell clones were isolated, many contained high constitutive luciferase activity, possibly due to integration of the plasmid (or a truncated form of the plasmid) into a genomic site which allows the promoter to be continually active. Since resistance to G418 of the isolated clones only indicates that each contains the neomycin resistant (neo) gene, the presence of intact/functional (inducible) pGudLuc1.1 DNA in all of the clones was confirmed by measurement of TCDD-inducible luciferase activity in each of the clones. The clones with the greatest ratio of inducible to constitutive luciferase activity were selected for further characterization.

More particularly, isolated clones were grown until confluent, and then incubated in the absence or presence of TCDD (1 nM solubilized in DMSO) for 24 hours. After the incubation, luciferase activity was determined as described above. TCDD treatment of these stably transfected cell lines revealed a significant induction of luciferase activity (between 14- and 74-fold) in each of the five isolated clones, as summarized in Table 2.

TABLE 2

TCDD-Inducible Luciferase Activity of Five
Clonal Cell Lines Stably Transfected with the
Expression Vector, pGudLuc1.1

| Cell line | Luciferase activity (RLU/mg protein)* | | Fold induction |
|---|---|---|---|
| | DMSO | TCDD in DMSO | |
| Mouse | | | |
| H1L1.1 | 0.08 ± 0.01 | 5.92 ± 0.70 | 74 |
| MLEL1.1c1 | 0.02 ± 0.01 | 0.29 ± 0.05 | 14 |
| Rat H4L1.1c4 | 0.02 ± 0.01 | 0.49 ± 0.03 | 25 |
| Guinea pig G16L1.1c8 | 0.03 ± 0.01 | 0.76 ± 0.03 | 25 |
| Human HG2L1.1c3 | 0.87 ± 0.07 | 25.04 ± 1.88 | 29 |

*Values are the mean ± the standard deviation of triplicate assays.

It is noted that of the majority of the stable TCDD-responsive cell lines that were initially isolated, only a few maintained their responsiveness for an extended time. In particular, the TCDD responsiveness of one Hepa1 clonal (H1L1.1) line was stably maintained for over 3 years, and the TCDD responsiveness of each of the MLE/BV (MLEL1.1c1), H4IIE (H4L1.1c4), GPC16 (G16L1.1c8), and HepG2 (HG2L1.1c3) clonal lines was stably maintained for at least 6–12 months. This phenomenon has been previously observed with other stably transfected cell lines (see, El-Fouly et al., supra) and underscores the importance of continual testing of transfectants for stability.

Since the mouse H1L1.1 line was the most highly inducible and its responsiveness was maintained for a longer time than the responsiveness of the other cell lines, the mouse H1L1.1 line was characterized in greater detail.

Figure 2:
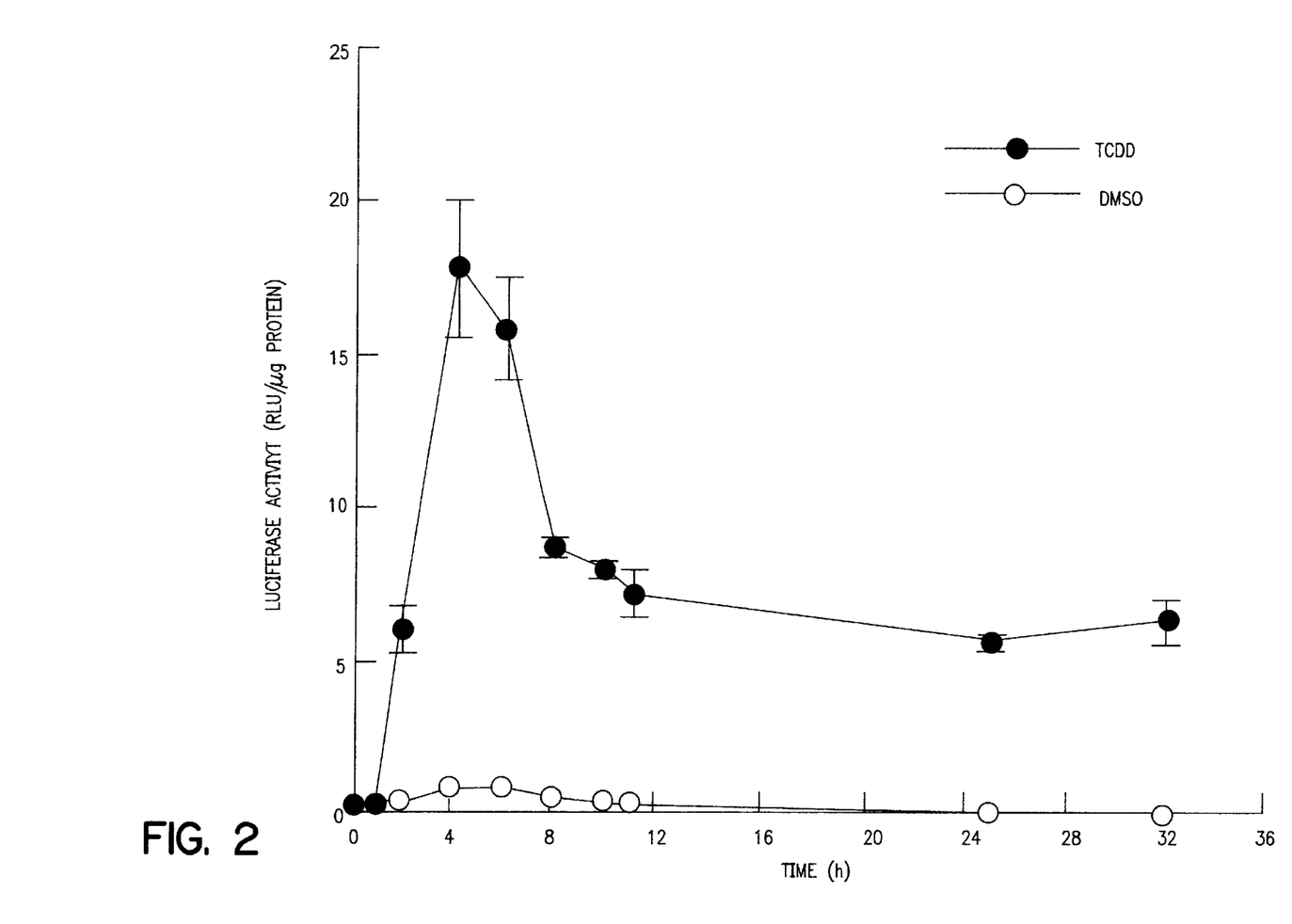
FIG. 2 is a graph showing the time course curve for induction of luciferase activity in H1L1.1 cells by TCDD.

Specifically, with respect to the graph of FIG. 2, the time course of luciferase induction by TCDD was examined in order to determine the optimal time period for measurement of luciferase activity in the H1L1.1 cells. In these experiments, the cells were treated with 1 nM of TCDD solubilized in DMSO or with only DMSO. The luciferase activity was determined as described above at various times up to 32 hours post exposure. Values represent the mean ± the standard evaluation of at least triplicate determinations.

As can be seen from the graph of FIG. 2, TCDD-inducible luciferase activity in the mouse H1L1.1c cells was detectable at 2 hours, peaked at about 4 hours, and then decreased to a stable activity by 12 hours after TCDD treatment. Therefore, although the absolute inducible luciferase activity in these cells varies with time, they can be used for the rapid (<4 hour) detection of the presence of TCDD and dioxin-like compounds.

Figure 3:
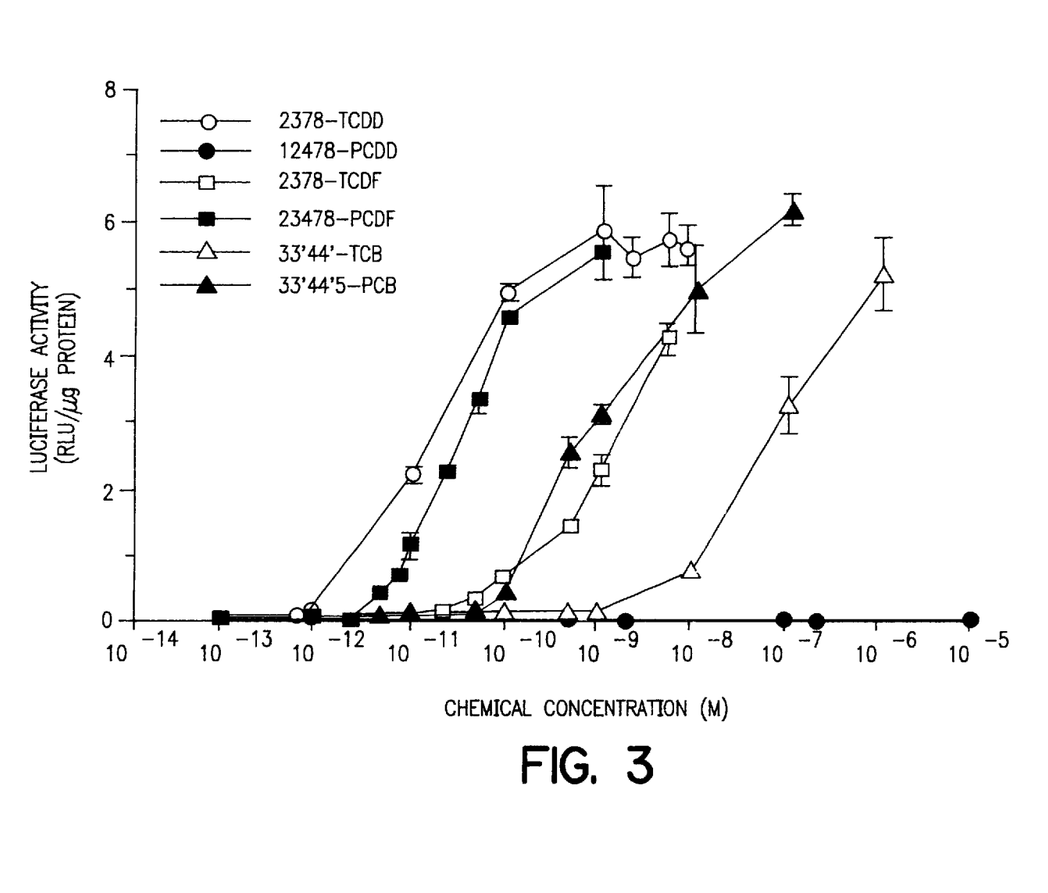
FIGS. 3 through 6, inclusive, are graphs showing dose response curves for the induction of luciferase activity in H1L1.1 cells by increasing concentrations by various chemicals.

The graph of FIG. 3 illustrates the dose dependence of luciferase induction in the mouse H1L1.1 cells measured following 24 exposures of the cells to increasing concentrations of TCDD or other toxic compounds (which others are discussed in more detail below).

More particularly, the stable cell clones for the mouse H1L1.1 cells (about 90% confluent) were plated into six-well microplates (purchased from Corning) and incubated for 24 hours with the indicated concentration of the particular toxin solubilized in DMSO. Then, the cells were lysed with 100 µl of lysis buffer and luciferase activity was determined as described above. Values represent the mean ± the standard evaluation of at least triplicate determinations.

As can be seen from the curve for TCDD (i.e., from the curve denoted with circles on the left side of the graph of FIG. 3), the utility of the mouse H1L1.1 cell line as a bioassay system for detection and relative quantitative analysis of TCDD is based upon not only this mouse cell line's sensitivity, specificity, and rapidity, but also its dose-dependent nature. Specifically, induction of luciferase activity in this mouse cell line was dose dependent, with a maximal induction (80-fold) by 1.0 nM TCDD.

As set out in Table 3, the responsiveness and sensitivity of the mouse H1L1.1 cells was compared to the responsiveness and sensitivity of certain other published PCDH cell bioassay systems. The other systems were a recombinant HepG2 (101L) cell line that induces firefly luciferase (see, Postlind et al., supra), a recombinant Hepa1 (T13) cell line that induces PAP activity (see El-Fouly et al., supra), and a rat H4IIE cell line that induces EROD activity (see, Kennedy et al., supra). The ED50 values were calculated by probit analysis of the dose-response data.

TABLE 3

Comparison with the Current Cell/Gene Expression-Based
Bioassays for Detection of TCDD-like Chemicals

| Cell bioassay | Gene | ED50 (nM) | MDL (pM) | Reference |
|---|---|---|---|---|
| Rat H4IIE (comparison) | CYP1A1/EROD | 0.1 | 10 | Kennedy et al. |
| Mouse T13 (comparison) | Alkaline phosphatase | 0.35 | 100 | El-Fouly et al. |
| Human 101L | Luciferase | 0.35 | 1 | Postlind |

TABLE 3-continued

Comparison with the Current Cell/Gene Expression-Based
Bioassays for Detection of TCDD-like Chemicals

| Cell bioassay | Gene | ED50 (nM) | MDL (pM) | Reference |
|---|---|---|---|---|
| (comparison) Mouse H1L1.1 (present invention) | Luciferase | 0.02 | 0.1–1 | et al. |

Although the estimated ED50 of these bioassays were all within an order of magnitude (0.02 to 0.35 nM), the MDLs for TCDD were less for the luciferase bioassay systems in the H1L1.1 (0.1 to 1 pM) and 101L (1 pM) cell lines than in the H4IIE (10 pM) and T13 (100 pM) cell lines. While it is not intended to be bound to any theory, it is believed that the significant difference in MDLs among these cell lines likely results from inherent differences in the sensitivities of the analytical methodology used for measurement of the respective enzyme activities rather than significant differences in inherent inducibility among these cell lines.

Furthermore, it is noted that the results reported in Table 3 for the 101L cells are significantly different from those reported by Postlind et al., supra, who stably transfected a PCDH-inducible luciferase reporter construct into human HepG2 (101L) cells. In their time-course experiments, induced luciferase activity did not drop off as rapidly as observed for the comparison data of the 101L cells with the present invention. While it is not intended to be bound to any theory as to what accounts for the difference in time course of induction/stability of luciferase between the two cell lines, the following is believed to be the reason. These cell lines are similar (mouse hepatoma source for the present invention and human hepatoma source for Postlind et al., supra). Therefore, it is believed that the difference between the present results and those of Postlind et al., supra, likely reflects differences in the specific expression vector constructs used in both experiments. Moreover, since prior art studies have indicated that firefly luciferase can be relatively unstable in certain mammalian cells, it is hypothesized that this transient peak in luciferase activity in the mouse H1L1.1 cells may be due to a time-dependent stimulation of luciferase degradation by cellular proteins.

As set out in the graphs of FIGS. 3–6, since one use of the stably transfected mouse H1L1.1 cell lines is for detection and relative quantitative analysis of TCDD and various dioxin-like compounds (i.e., AhR ligands), the ability of various compounds besides TCDD to induce luciferase activity in the mouse H1L1.1 cells was examined. The experiments performed to determine the dose-response curves for the toxins other than TCDD set out in the graphs of FIGS. 3–6 were performed in essentially the same manner as the experiments described above to determine the dose response curve of TCDD set out in the graph of FIG. 3.

Figure 4:
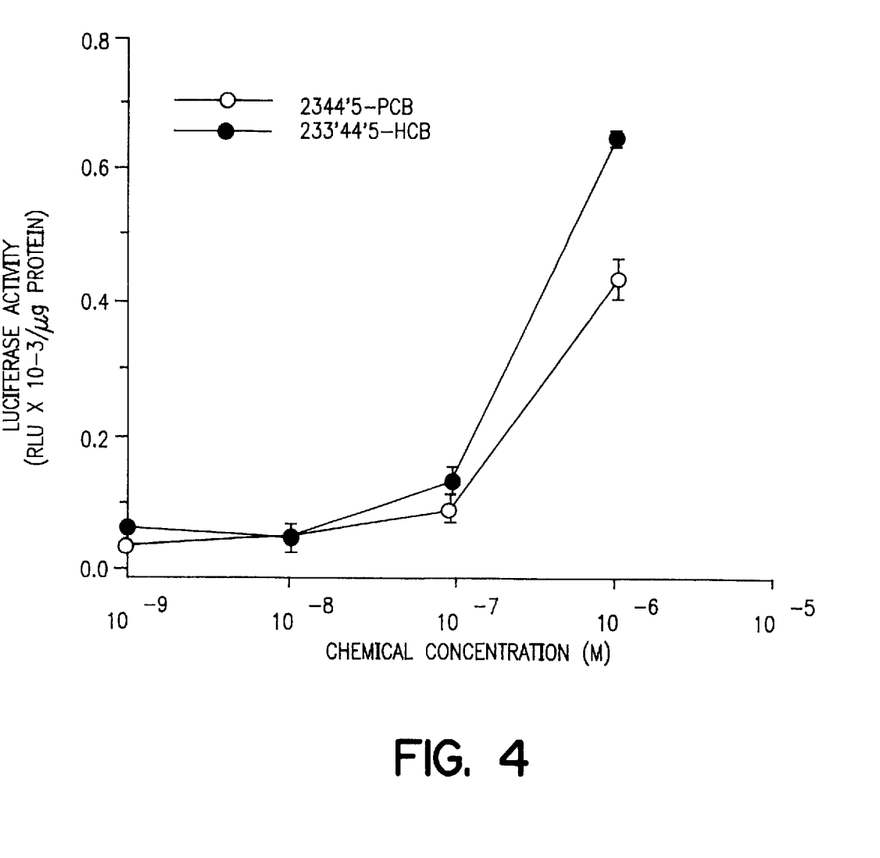
Figure 5:
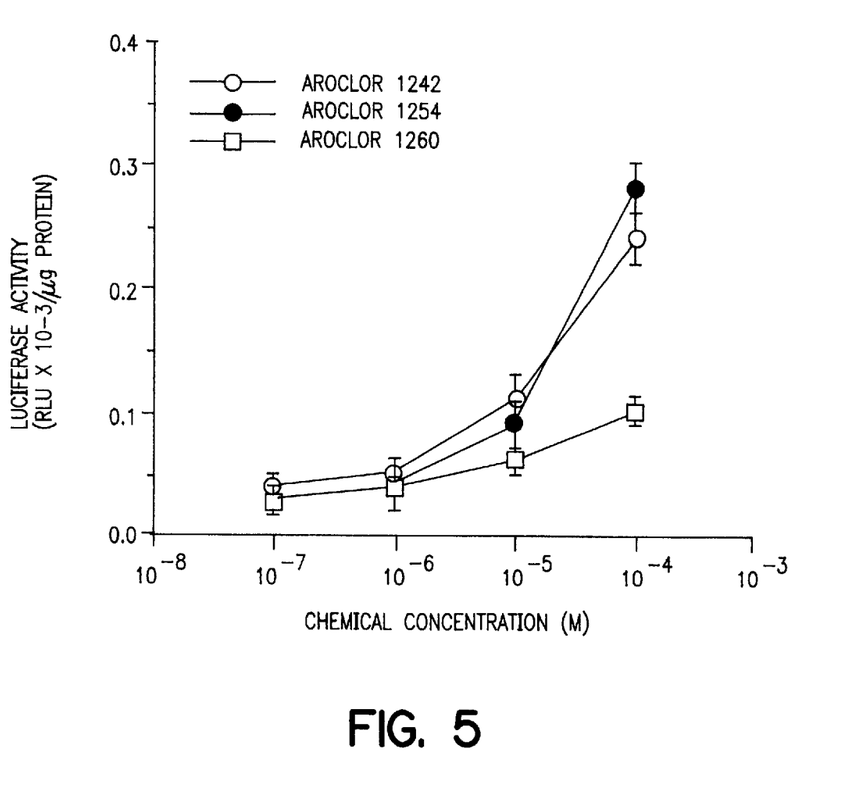
Figure 6:
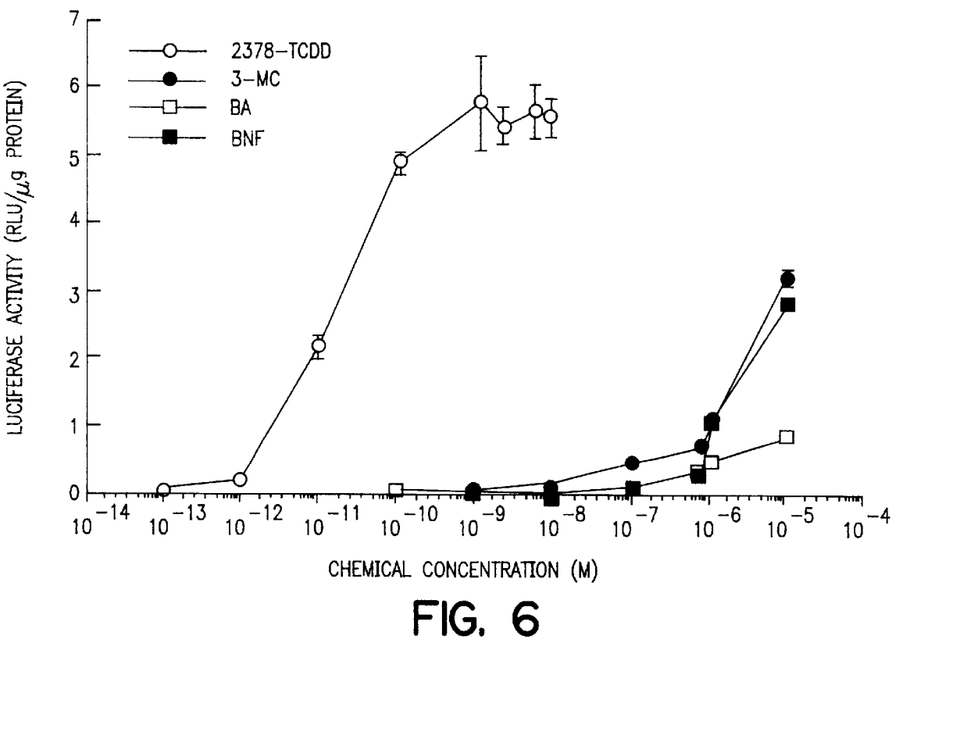

The toxins reported for the various graphs of FIGS. 3–6 were as follows. The graph of FIG. 3 illustrates TCDD, 2,3,7,8-TCDF, 2,3,4,7,8-PCDF, 1,2,4,7,8-PCDD, 3,3',4,4',5-PCB, and 3,3',4,4'-TCB. The graph of FIG. 4 illustrates 2,3,3',4,4',5-HCB and 2,3,4,4',5-PCB. The graph of FIG. 5 illustrates AROCLOR 1242, AROCLOR 1254, and AROCLOR 1260. The graph of FIG. 6 illustrates TCDD, 3-MC, BA, and BNF.

Specifically, with respect to the data illustrated in the graph of FIG. 3, cells were incubated with increasing concentrations of test chemical and luciferase activity determined after 24 hours. Luciferase activity was induced to comparable levels by TCDD with an EC50 of about 20 pM, and by the "TCDD-like" PCDFs, namely 2,3,7,8-TCDF and 2,3,4,7,8-PCDF, with EC50s of about 50 pM and about 2 nM, respectively. Additionally, luciferase activity was induced to comparable maximal levels by the "TCDD-like" PCBs, namely 3,3',4,4',5-PCB and 3,3',4,4'-TCB, with EC50 values of 2 and 100 nM, respectively.

However, as also can be seen in the graph of FIG. 3, cells incubated with 1,2,4,7,8-PCDD showed no luciferase activation at concentrations up to 10 $\mu$M of 1,2,4,7,8-PCDD. This result is in contrast to prior art studies in rats and rat hepatoma cells, in which 1,2,4,7,8-PCDD was an active inducer, although 500- to 1000-fold less potent than TCDD (see, Safe, S. H., "Polychlorinated Biphenyls (PCBs): Environmental Impact, Biochemical and Toxic Responses and Implications for Risk Assessment", Crit. Rev. Toxicol., Vol. 24, pp. 87–149 (1994)). Although it is not intended to be bound to any theory as to the reason for the lack of induction by 1,2,4,7,8-PCDD in the mouse H1L1.1 cells, it is possible that this could be accounted for, at least in part, by species differences in AhR ligand binding and/or affinity.

Furthermore, as shown in the graph of FIG. 4, the lower potency TCDD-like mono-ortho-PCBs, namely, 2,3,3',4,4', 5-HCB and 2,3,4,4',5-PCB, induced moderate luciferase activity (10-fold, to 20–30% of that observed with TCDD). The relative luciferase induction potency in the mouse H1L1.1 cells by these two mono-ortho-substituted PCBs is comparable to their induction potency in rat hepatoma cells (see, Safe, supra).

Additionally, as can be seen from the graph of FIG. 5, moderate induction of luciferase activity (3- to 9-fold, to 10–30% of that observed with TCDD) was observed using AROCLOR 1242, 1254, and 1260. The relative induction potency of these mixtures of PCBs is comparable to that reported in previously published in vivo induction studies (see Safe, supra).

It should be noted that the low numerical values of luciferase activity from induction by various PCBs reported in FIGS. 4 and 5, compared to the values reported in the other figures, are not due to actual low levels of luciferase induction, but to the fact that the detection of luminescence in these experiments was performed using a different instrument from that used in the other experiments. Since the instrumental method of luminescence detection and quantitative analysis was different in each experiment, the actual numerical values obtained from each instrument are not directly comparable.

However, the relative magnitude of luciferase induction by the mono-ortho-PCBs (FIG. 4) and the AROCLORS (FIG. 5) was established by directly comparing the resulting activity to that produced by a maximally inducing dose of TCDD (1 nM solubilized in DMSO) measured in the same instrument. The specific TCDD induction result determined for the experiments shown in the graph of FIG. 4 for 2,3,4,4',5-PCB and 2,3,3',4,4',5-HCB was an induced luciferase activity of 2.25±0.6; and the specific TCDD induction result determined for the experiments shown in the graph of FIG. 5 for AROCLOR 1242, 1254, and 1260 (chemical concentration was based on calculations using the average molecular weight of the particular PCB contained in the mixture) was an induced luciferase activity of 0.95±0.07.

Thus, maximal levels of luciferase induction by various TCDD-like compounds (i.e., AhR ligands), similar to the levels by TCDD, are observed with the present invention, which is in contrast to the report of Kennedy et al., supra, for induction of EROD activity, where numerous AhR ligands (i.e., various PCBs) not only fail to induce EROD activity maximally to levels comparable to that induced by TCDD, but also EROD activity actually decreases with higher concentrations of inducing agent. While it is not intended to be bound to any theory, it is postulated that the reduced EROD activity at higher inducer concentrations is due to the chemicals' ability to act as competitive substrate inhibitors of P4501A1 activity. Since some chemicals known to induce P4501A1 gene expression (via AhR binding) can also be substrates for the P4501A1 enzyme, utilization of the EROD assay for estimation of TCDD equivalents in sample extracts containing these chemicals could complicate accurate estimation of the amount of these chemicals in the sample extracts. Thus, the fact that these chemical inducers are not competitive substrates for the luciferase enzyme is another advantage of the bioassay of the present invention over that of EROD.

As shown in the graph of FIG. 6, the relative inducing potency of three fused-ring PAHs, namely, 3-MC, BA, and BNF, was also examined and the data indicated that these chemicals were substantially less potent than TCDD. The results obtained in the present studies were comparable to the relative induction results reported by Postlind et al., supra, although their bioassay system appeared to be slightly more sensitive to induction by BA. Additionally, it should be noted that in these experiments with 3-MC, BA, and BNF, maximal luciferase expression was not reached. The reason for not reaching maximal expression is that although increasing the concentration of these inducing chemicals in DMSO will result in significantly higher levels of induction (data not shown), the solubility of these chemicals in DMSO at higher concentrations is questionable.

Figure 7:
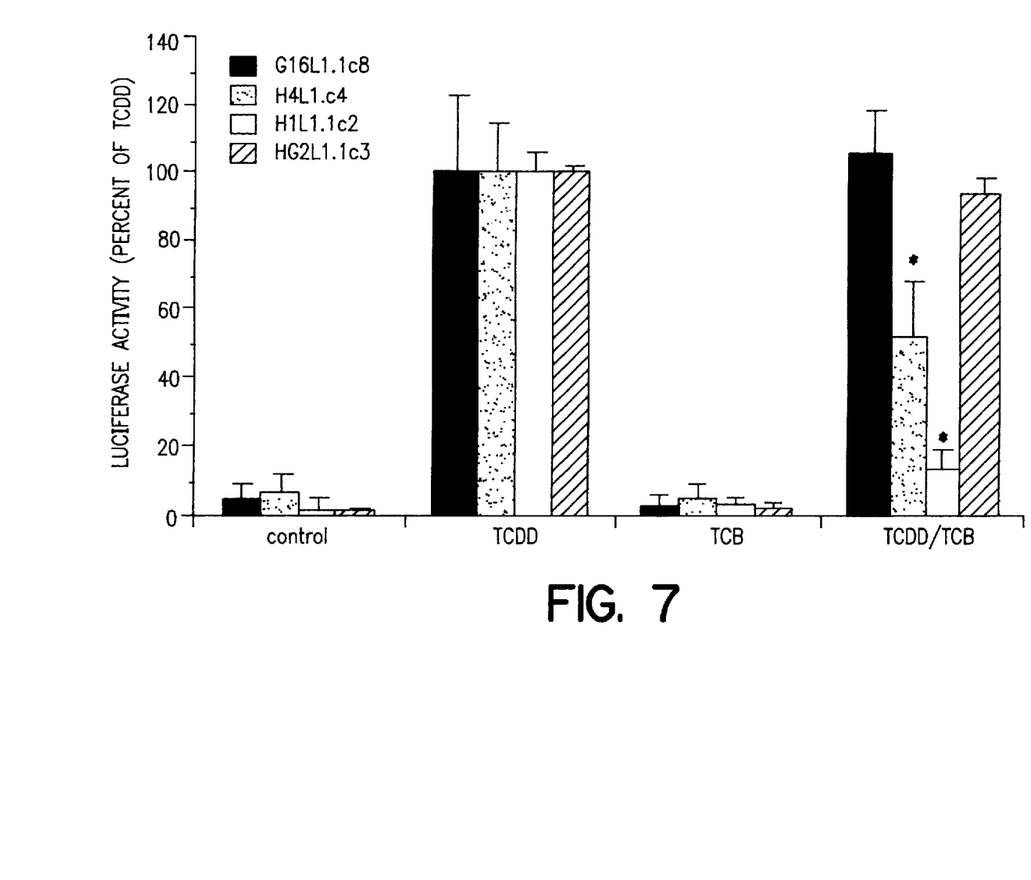
FIG. 7 is a graph showing that 2,2',5,5'-tetrachlorobiphenyl antagonizes induction of luciferase activity by TCDD in a species specific manner.

The bar graph of FIG. 7 illustrates that 2,2',5,5'-TCB antagonizes induction of luciferase activity by TCDD in a species-specific manner, and thus, 2,2',5,5'-TCB is not a TCDD-like compound as defined herein. In particular, six-well plates containing the indicated cell lines were incubated with DMSO (control), with TCDD (5 nM), with 2,2',5,5'-TCB (25 $\mu$M), or with both TCDD (5 nM) and 2,2',5,5'-TCB (25 $\mu$M) for 24 hours. Luciferase activity in cell lysates was determined as described above. Values represent the mean ± the standard evaluation of at least triplicate determinations.

Therefore, the utility of these bioassays in examining species-specific differences in responsiveness was demonstrated by examining the effect of 2,2',5,5'-TCB on the ability of TCDD to induce luciferase activity in the stably transfected guinea pig G16L1.1c8, rat H4L1.1 c4, mouse H1L1.1, and human HG2L1.1c3 cell lines described above. Exposure to TCDD (5 nM) alone induced luciferase activity in all cell lines while exposure to 2,2',5,5'-TCB (25 $\mu$M) alone had no significant effect. Although induction of luciferase activity by TCDD in guinea pig and human cells was not affected by coadministration of TCDD and 2,2',5, 5'-TCB, significantly less luciferase induction was observed in the rat and mouse cell lines (reduced by 47 and 86%, respectively).

Detailed biochemical and molecular analysis of this apparent species difference in antagonism has demonstrated that it is due to the differential ability of 2,2',5,5'-TCB competitively to inhibit TCDD binding to the mouse and rat AhRs but not to the guinea pig and human AhRs. In other words, since the DNA regulatory elements controlling expression of the luciferase gene are identical in each of the stably transfected cell lines, the differences in responsiveness of the cell lines are the result of species differences in the AhR, its associated proteins, and/or trans-acting factors present in each cell type. These results also demonstrate that the ligand binding specificity of the AhR is not identical among species. Thus, these cell lines provide useful model systems for examining species differences in response to TCDD-like compounds.

Figure 8:
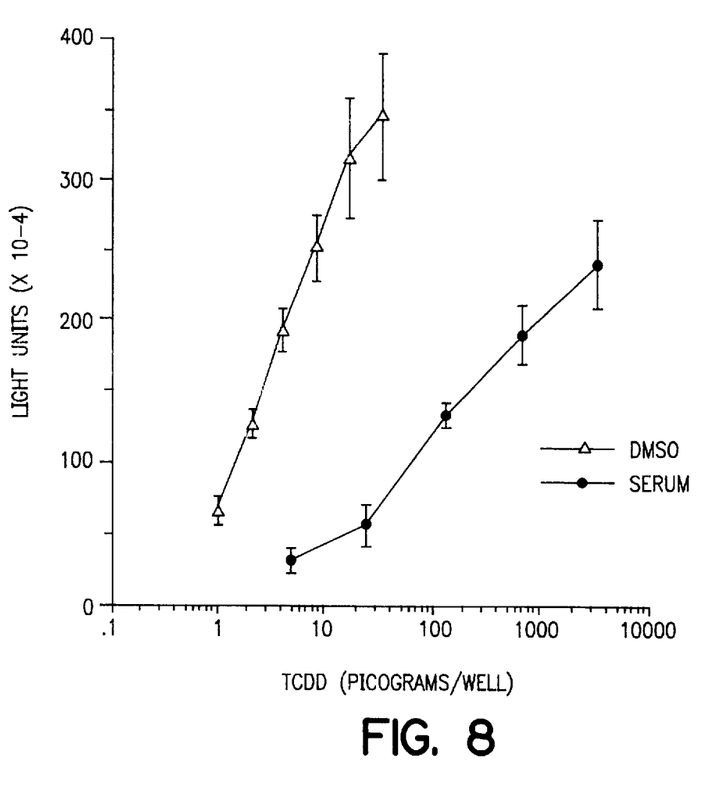
FIG. 8 is a graph showing dose response curves for induction of luciferase activity in H1L1.1 cells incubated with the indicated concentration of either TCDD dissolved in DMSO or TCDD dissolved in serum.

The graph in FIG. 8 shows dose response curves for induction of luciferase in mouse H1L1.1 cells incubated with the indicated concentration of TCDD dissolved in DMSO or TCDD dissolved in serum. Specifically, since it is desired to utilize the present bioassay system directly to detect PAHs in samples without the need for solvent extraction and concentration, the dose-dependence of luciferase induction in cells incubated with increasing concentrations of TCDD in serum versus that observed with increasing concentrations of TCDD in DMSO was examined. In other words, the present bioassay system should be advantageously employed directly with a sample of serum from an animal or human, where the sample may contain TCDD or other PAHs and the serum is the solvent, whereby solvent extraction of the sample with DMSO as the solvent is unnecessary.

The cells were incubated with the respective increasing concentrations of TCDD for 4 hours and luciferase activity of cell lysates determined as follows.

More particularly, mouse H1L1.1 cells were grown in 10% fetal calf serum (purchased from Atlanta Biologicals) in RPMI 1640 media (purchased from Gibco) in T flasks to near confluence and then harvested with trypsin. The cells were washed in saline containing 10% fetal calf serum, resuspended to a concentration of $1.25 \times 10^6$ cells/ml, plated in 100 $\mu$l volumes in Dynatech 96-well viewplates, and incubated overnight at 37° C. in a 4.8% humidified atmosphere of $CO_2$.

Chemical treatment was carried out by direct addition of TCDD-containing serum to these cultures or direct addition of TCDD-containing DMSO (1 $\mu$l/100 $\mu$l media) to the wells in triplicate followed by plate mixing on a microplate vortexer. The cultures were incubated for 4 hours at 37° C., followed by washing of the cells with saline and addition of 100 $\mu$l of cell lysis buffer (25 mM of tris phosphate, pH 7.8, 2 mM of dithiothreitol, 2 mM of 1,2-diaminocyclohexane-N,N,N'N'-tetracetic acid, 10% glycerol, and 1% Triton X-100).

After incubation for an additional 15 minutes, luciferase activity in the lysed cells was determined. Luciferase activity was sensitively measured using its bioluminescent substrate, luciferin in a Dynatech ML3000 microplate luminometer. In these experiments, cells either kept intact or lysed using luciferase lysis buffer (purchased from Promega) and luciferase activity in an aliquot of the lysate was determined by automatic injection of assay reagent and measurement of the resulting bioluminescence. Comparison of the enzymatic activity present in untreated samples to that in the treated samples revealed the degree of inducibility.

The results demonstrate that the addition of TCDD-containing serum samples to the present recombinant cells can induce expression of luciferase activity in a dose-dependent manner. The relative potency (ED50) for luciferase induction was significantly lower for the TCDD-serum sample than for the TCDD-DMSO sample. A significant response over background was observed at serum concentrations of TCDD above 50 pM. This corresponds to a concentration of approximately 16 ppt TCDD in the serum sample and is about 1–2 orders of magnitude less sensitive than the assay of TCDD in DMSO (<1 pg), presumably due to serum binding of the chemical. Hence, the bioassay of the invention can be employed directly with a sample of serum from an animal or human, with the sample containing TCDD or other PAHs and with the serum as the solvent, as a result of which solvent extraction of the sample with DMSO as the solvent is not needed.

Also, the detection limits of the assay depend upon the volume of serum used in the analysis. For instance, extraction of 1 ml of serum applied in DMSO gives a detection limit of about 1 pg/ml or 1 ppt; however, if 10 ml of serum were extracted, the present detection limits would be about 0.1 pg/10 ml or 0.1 ppt. Since the average background level of TCDD in human serum is 10–20 ppt on a lipid adjusted basis, the 96-well bioassay (using solvent extracted PCDHs) should be capable of detecting TCDD at levels of 1 order of magnitude below background levels, and is in fact more sensitive than is required in order to detect TCDD exposure in human serum. In short, it can be seen from FIG. 8 that the bioassay of the present invention has a sensitivity of 100 parts per quadrillion of TCDD.

In summary, a PAH-inducible reporter plasmid, pGudLuc1.1, has been constructed that responds to TCDD and to TCDD-like compounds in a dose-, time-, and AhR-dependent manner with the induction of firefly luciferase. The approach described here for production of a bioassay based on the activity of a ligand-dependent transcriptional factor has much broader applications.

More particularly, the biological response elicited in these bioassays will allow identification of the presence of bioactive compounds in a sample relatively quickly and indicate if further analysis, such as gas chromatography and/or mass spectrometry, should be performed. Additionally, a sensitive and inexpensive bioassay, such as the one described here, could be readily utilized for a variety of screening purposes, such as providing a relative measure of the level of toxic bioactive TCDD-like compounds and/or TCDD in food, biological (i.e., blood), or environmental samples and a relative measure of the effectiveness of remediation procedures designed to decrease levels of toxic bioactive TCDD-like compounds and/or TCDD.

It will be understood that various details of the invention may be changed without departing from the scope of the invention. Furthermore, the foregoing description is for the purpose of illustration only, and not for the purpose of limitation—the invention being defined by the claims.

What is claimed is:

1. A recombinant cell line deposited at the American Type Culture Collection under ATCC accession number CRL-12286 and known as the mouse H1L1.1c2 cell line, which will respond to selected polyaromatic hydrocarbon compounds with expression of luciferase activity.

2. The recombinant cell line of claim 1, wherein the polyaromatic hydrocarbon compounds are selected from the group consisting of polychlorinated dibenzo-para-dioxins, 2,3,7,8-tetrachlorodibenzo-para-dioxin (TCDD)-like compounds, and combinations thereof.

3. The recombinant cell line of claim 2, wherein the polychlorinated dibenzo-para-dioxin is 2,3,7,8-tetrachlorodibenzo-para-dioxin.

4. The recombinant cell line of claim 2, wherein the TCDD-like compounds are selected from the group consisting of TCDD-like fused-ring polyaromatic hydrocarbon compounds, TCDD-like polychlorinated di-aromatic hydrocarbon compounds, and combinations thereof.

5. The recombinant cell line of claim 4, wherein the TCDD-like fused-ring polyaromatic hydrocarbon compounds are selected from the group consisting of benz[a]anthracene, β-naphthoflavone, 3-methylcholanthrene, and combinations thereof.

6. The recombinant cell line of claim 4, wherein the TCDD-like polychlorinated di-aromatic hydrocarbon compounds are selected from the group consisting of polychlorinated dibenzofuran compounds, coplanar polychlorinated biphenyl compounds, and combinations thereof.

7. The recombinant cell line of claim 6, wherein the polychlorinated dibenzofuran compounds are selected from the group consisting of 2,3,7,8-tetrachlorodibenzofuran, 2,3,4,7,8-pentachlorodibenzofuran, and combinations thereof.

8. The recombinant cell line of claim 6, wherein the coplanar polychlorinated biphenyl compounds are selected from the group consisting of 3,3',4,4'-tetrachlorobiphenyl, 3,3',4,4',5-pentachlorobiphenyl, 2,3,4,4',5-pentachlorobiphenyl, 2,3,3',4,4',5-hexachlorobiphenyl, and combinations thereof.

9. The recombinant cell line of claim 1, wherein the cell line comprises a mouse hepatoma cell line transfected with a recombinant expression plasmid, wherein the recombinant expression plasmid includes dioxin responsive elements upstream of a luciferase gene.

10. The recombinant cell line of claim 1, wherein the polyaromatic hydrocarbon compound is 2,3,7,8-tetrachlorodibenzo-para-dioxin contained in a certain amount in a sample and the lowest amount of 2,3,7,8-tetrachlorodibenzo-para-dioxin that can be detected by the expression of luciferase activity by the mouse H1L1.1c2 cell line is about 100 parts of 2,3,7,8-tetrachloro-dibenzo-para-dioxin per quadrillion parts of the sample.

11. A method for the quantitative analysis of selected polyaromatic hydrocarbon compounds in samples, the method comprising the steps of:

(a) providing a sample containing a suspected amount of at least one of said polyaromatic hydrocarbon compounds; and (b) determining the amount of said polyaromatic hydrocarbon compound present in the sample by using a recombinant cell line deposited at the American Type Culture Collection under ATCC accession number CRL-12286 and known as the mouse H1L1.1c2 cell line.

12. The method of claim 11, wherein in step (a), the sample contains said polyaromatic hydrocarbon compound solubilized in a solvent.

13. The method of claim 12, wherein in step (a), the solvent dissolves said polyaromatic hydrocarbon compound and is free of toxicity to the recombinant cell line.

14. The method of claim 13, wherein in step (a), the solvent is at least one of dimethyl sulfoxide and fetal calf serum.

15. The method of claim 11, wherein in step (a), the polyaromatic hydrocarbon compound is selected from the group consisting of polychlorinated dibenzo-para-dioxins, 2,3,7,8-tetrachlorodibenzo-para-dioxin (TCDD)-like compounds, and combinations thereof.

16. The method of claim 15, wherein the polychlorinated dibenzo-para-dioxin is 2,3,7,8-tetrachlorodibenzo-para-dioxin.

17. The method of claim 15, wherein the TCDD-like compounds are selected from the group consisting of TCDD-like fused-ring polyaromatic hydrocarbon compounds, TCDD-like polychlorinated di-aromatic hydrocarbon compounds, and combinations thereof.

18. The method of claim 17, wherein the TCDD-like fused-ring polyaromatic hydrocarbon compounds are selected from the group consisting of benz[a]anthracene, β-naphthoflavone, 3-methylcholanthrene, and combinations thereof.

19. The method of claim 17, wherein the TCDD-like polychlorinated di-aromatic hydrocarbon compounds are selected from the group consisting of polychlorinated dibenzofuran compounds, coplanar polychlorinated biphenyl compounds, and combinations thereof.

20. The method of claim 19, wherein the polychlorinated dibenzofuran compounds are selected from the group consisting of 2,3,7,8-tetrachlorodibenzofuran, 2,3,4,7,8-pentachlorodibenzofuran, and combinations thereof.

21. The method of claim 19, wherein the coplanar polychlorinated biphenyl compounds are selected from the group consisting of 3,3',4,4'-tetrachlorobiphenyl, 3,3',4,4',5-pentachlorobiphenyl, 2,3,4,4',5-pentachlorophenyl, 2,3,3',4,4',5-hexachlorobiphenyl, and combinations thereof.

22. A method for the quantitative analysis of selected polyaromatic hydrocarbon compounds in samples, the method comprising the steps of:
 (a) providing a sample containing a suspected amount of at least one of said polyaromatic hydrocarbon compounds; and
 (b) determining the amount of said polyaromatic hydrocarbon compound present in the sample by using a recombinant cell line deposited at the American Type Culture Collection under ATCC accession number CRL-12286 and known as the mouse H1L1.1c2 cell line, wherein the determining of the amount of said polyaromatic hydrocarbon compound present in the sample is accomplished in about 8 hours or less.

23. The method of claim 22, wherein in step (b), determining the amount of said polyaromatic hydrocarbon compound present in the sample is accomplished in about 6 hours or less.

24. The method of claim 23, wherein in step (b), determining the amount of said polyaromatic hydrocarbon present in the sample is accomplished in about 4 hours or less.

25. The recombinant cell line of claim 1, wherein the recombinant cell line is capable of responding to selected polyaromatic hydrocarbon compounds with expression of luciferase activity in about 8 hours or less.

26. The recombinant cell line of claim 25, wherein the recombinant cell line is capable of responding to selected polyaromatic hydrocarbon compounds with expression of luciferase activity in about 6 hours or less.

27. The recombinant cell line of claim 26, wherein the recombinant cell line is capable of responding to selected polyaromatic hydrocarbon compounds with expression of luciferase activity in about 4 hours or less.

28. The method of claim 11, wherein the sample comprises a serum sample.

29. The method of claim 28, wherein in step (b), determining the amount of said polyaromatic hydrocarbon compound present in the serum sample is accomplished in about 8 hours or less.

30. The method of claim 29, wherein in step (b), determining the amount of said polyaromatic hydrocarbon compound present in the serum sample is accomplished in about 6 hours or less.

31. The method of claim 30, wherein in step (b), determining the amount of said polyaromatic hydrocarbon present in the serum sample is accomplished in about 4 hours or less.

* * * * *